(12) United States Patent
Blakemore et al.

(10) Patent No.: US 6,703,522 B2
(45) Date of Patent: Mar. 9, 2004

(54) ALKYL AMINO ACID DERIVATIVES USEFUL AS PHARMACEUTICAL AGENTS

(75) Inventors: David Clive Blakemore, Cambridge (GB); Justin Stephen Bryans, Balsham (GB); Sophie Caroline Williams, Cambridge (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/301,295

(22) Filed: Nov. 21, 2002

(65) Prior Publication Data

US 2003/0144214 A1 Jul. 31, 2003

Related U.S. Application Data

(63) Continuation of application No. 09/920,215, filed on Aug. 1, 2001, now abandoned.

(51) Int. Cl.[7] .............................................. C07C 26/00
(52) U.S. Cl. ...................................................... 560/157
(58) Field of Search ......................................... 560/157

(56) References Cited

FOREIGN PATENT DOCUMENTS

| WO | WO 98/09957 | * | 3/1998 |
| WO | WO 99/31074 | * | 6/1999 |

OTHER PUBLICATIONS

Brenner et al, Helvetica Chimica Acta vol. 82, 1999 pp. 2365–2379.*
Slavinskaya et al Zh Org Zhin vol. 32, 1996 pp 1683–1684.*
Co–pending U.S. application No. 10/009,938.
Co–pending U.S. application No. 09/254,093.
Great Britain Search Report GB 0018828.4.
Brenner and Seebach, Enantioselective Preparation of gamma.–amino acids and .gamma.–lactams from nitro olefins and carboxylic acids, with the valins–derived 4–isopropyl–5,5–diphenyl–1,3–oxazolidin–2–one as an auxiliary, Chemical Abstract No. 132:194314.
Barluenga et al., Cycloaddition Reactions of Chiral 2–Amino–1,3–butadienes with Nitroalkenes: Synthesis of Enantiomerically Pure 4–Nitrocyclohexanones, Chemical Abstract No. 127:205290.
Larue et al., Solution conformation of .alpha., .beta. or .gamma.–methylglutamyl–containing derivatives as probes of vitamin K–dependent carboxylase using molecular modeling and nuclear magnetic resonance, Chemical Abstract No. 127:118890.
Dieter et al., (.alpha.–Aminoalkyl) cuprates Prepared from Soluble Copper (I) Salts: Conjugate Additions to .alpha., .beta.–Unsaturated Carboxylic Acid Derivatives, Chemical Abstract No. 127:33680.
Slavinskaya et al., Synthesis of 4–amino–3–phenylburanohydroxamic acid, Chemical Abstract No. 126:277230.
Leenders et al., .beta.–Glucuronyl carbamate based pro–moieties designed for prodrugs in ADEPT, Chemical Abstract No. 123:228716.
Bryan et al., Facile synthesis of .beta.–substituted glutamic acids, Chemical Abstract No. 122.10509.
Suzuki et al., thero–3–Alkyl– and –arylglutamic acid derivatives by Michael additions of Boc–BMI Li–enolates to 2, 6–di–tert–butyl–4–methoxyphenyl alkenoates on the diastereoselectivity of the coupling of trigonal centers involving heterocyclic Li–enolates, Chemical Abstract No. 116:84124.
Andruszkiewicz et al., 4–Amino–3–alkybutanoic acids as substrates for .gamma. –aminobutyric acid aminotransferase, Chemical Abstract No. 114:7161.
Andruszkiewicz et al., Chemoenzymatic synthesis of (R)–and (S)–4–amino–3–methylbutanoic acids, Chemical Abstract No. 113:41263.
El Achqar et al., 2–Hydroxy–3–pinanone as chiral auxiliary in the asymmetric synthesis of .alpha. –amino acids, Chemical Abstract No. 110:193343.
Sivov et al., Preparing (+)—or (–)—.beta.–phenyl–.gamma.–aminobutyric acid hydrochlorides, Chemical Abstract No. 95:203556.

* cited by examiner

Primary Examiner—Paul J. Killos
(74) Attorney, Agent, or Firm—Charles W. Ashbrook; David R. Kurlandsky

(57) ABSTRACT

GABA-related pro-drugs of the formula (III) are provided that when administered to humans or other mammals provide an increased duration of active compound in the plasma compared to compounds of corresponding structure in which labile groups are not present. The compounds are of the formula (III)

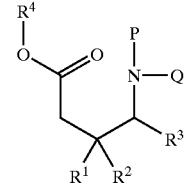

(III)

In the above formula:

P represents hydrogen or methyl;

Q represents a labile amine- or amide-forming organic group that becomes removed in the human or animal body;

$R^1$ represents straight or branched $C_2$–$C_6$ alkyl, $C_3$–$C_6$ cycloalkyl or phenyl;

$R^2$ represents hydrogen or methyl; and $R^3$ represents hydrogen, methyl or carboxyl; and $R^4$ represents hydrogen or a labile ester-forming group selected from substituted and unsubstituted $C_1$–$C_6$ alkyl, benzyl and phenyl groups that become removed in the human or animal body. In the above formula when $R^1$ is phenyl, $R^2$, $R^3$ and $R^4$ are not simultaneously hydrogen. Pharmaceutically acceptable salts of any salt-forming compound within the above class are also included. The compounds may be used to treat a range of neurological conditions, e.g. epilepsy and pain.

17 Claims, No Drawings

ALKYL AMINO ACID DERIVATIVES USEFUL AS PHARMACEUTICAL AGENTS

This is a continuation of application Ser. No. 09/920,215 filed Aug. 1, 2001 now abandoned.

FIELD OF THE INVENTION

This invention relates to novel alkyl amino acid derivatives useful as pharmaceutical agents, to processes for their production, to pharmaceutical compositions containing them, and to their use for the treatment of the neurological conditions set out below.

BACKGROUND TO THE INVENTION

U.S. Pat. No. 5,563,175 describes compounds of the formula (I)

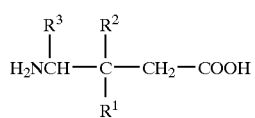

in which:

R$^1$ represents straight or branched C$_1$–C$_6$ alkyl, C$_3$–C$_6$ cycloalkyl or phenyl;

R$^2$ represents hydrogen or methyl; and

R$^3$ represents hydrogen, methyl or carboxyl.

The compounds (including their pharmaceutically acceptable salts) are analogues of γ-aminobutyric acid (GABA) and were stated to activate GAD, to bind to a novel binding site, to be useful in anti-seizure therapy for central nervous system disorders such as epilepsy, Huntington's chorea, cerebral ischemia, Parkinson's disease, tardive diskinesia and spasticity, and also to exhibit antidepressant, anxiolytic and antipsychotic activity. The most preferred compounds were those where R$^3$ and R$^2$ were hydrogen and R$^1$ was isobutyl, the (S)-(+) enantiomer of formula (II) being the most preferred.

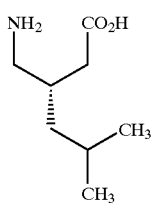

That compound is variously called 4-amino-3-(2-methylpropyl)butanoic acid, 3-(aminomethyl)-5-methylhexanoic acid, β-isobutyl-γ-aminobutyric acid, isobutyl-GABA, isobutylgaba and pregabalin.

U.S. Pat. No. 6,001,876 discloses that the above compounds are useful in pain therapy. U.S. Pat. No. 5,840,956 discloses methods for making (±)-isobutylgaba and for obtaining from it (S)-isobutylgaba. The disclosures of all the above patents are hereby incorporated by reference.

SUMMARY OF THE INVENTION

A problem with which this invention is concerned is the production of compounds useful in the manner of pregabalin, especially in pain therapy, that when administered to humans or other animals provide an increased duration of active ingredient in the plasma.

That problem is unexpectedly solved, according to the invention, by pro-drugs of pregabalin the compounds of the formula (III)

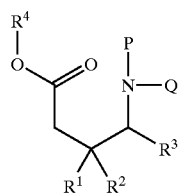

in which:

P is hydrogen or methyl;

Q is a labile amine- or amide-forming organic group that becomes removed in the human or animal body;

R$^1$ is straight or branched C$_2$–C$_6$ alkyl, C$_3$–C$_6$ cycloalkyl or phenyl;

R$^2$ is hydrogen or methyl; and

R$^3$ is hydrogen, methyl or carboxyl;

R$^4$ is hydrogen or a labile ester-forming group selected from substituted and unsubstituted C$_1$–C$_6$ alkyl, benzyl and phenyl groups that become removed in the human or animal body, and a pharmaceutically acceptable salt of any salt-forming compound within the above class, but excluding compounds in which R$_1$ is phenyl and R$^2$, R$^3$ and R$^4$ are each hydrogen.

It is believed that a pro-drug of the above formula when administered to a human or other animal, especially a mammal, enters the bloodstream by passive diffusion along the whole length of the intestine, which gives a much longer duration of effectiveness. The pro-drug may not itself be biologically active, but decomposes to the corresponding active compound in plasma.

Certain of the compounds of the invention can exist in unsolvated forms as well as solvated forms, including hydrated forms. In general, the solvated forms, including hydrated forms, are biologically equivalent to unsolvated forms and are encompassed within the scope of the invention. Certain of the compounds of the invention possess one or more chiral centers and each center may exist in the R or S configuration. The invention includes all enantiomeric and epimeric forms as well as the appropriate mixtures thereof. It also includes salts of any of the above compounds with physiologically acceptable cations or anions.

The invention also provides a method for making a compound of the formula (III) above, which comprises:

coupling a compound of the formula:

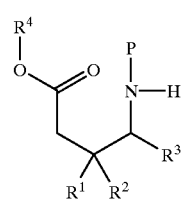

in which P and R$^1$–R$^4$ have the meanings given above and in which said compound is in the form of a free base or an ammonium salt with a compound of the formula (VI)

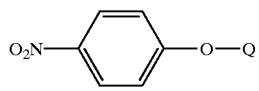

(VI)

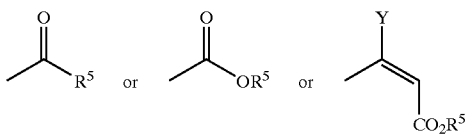

or QCl, where (in each case) Q has the meaning given above;

and the invention also provides a method for making a compound of the formula (III) above, which comprises coupling a compound of the formula (V) that is a carboxylic acid, optionally employing the further step of esterifying the carboxyl group with a substituted or unsubstituted $C_1$–$C_6$ alkanol, benzyl alcohol or phenol.

The invention also provides a pharmaceutical composition comprising a therapeutically effective amount of a compound of formula (III) above and a pharmaceutically acceptable carrier.

In a further aspect the invention provides the use of a compound of formula (III) in the manufacture of a medicament for the treatment of any of the following:

| | |
|---|---|
| epilepsy; | a faintness attack; |
| hypokinesia; | a cranial disorder; |
| a neurodegenerative disorder; | depression; |
| anxiety; | panic; |
| pain; | a neuropathological disorder; |
| | a digestive disorder. |

In a further aspect, the invention provides a method for treating any of the above disorders which comprises administering a therapeutically effective amount of a compound of formula (III) to a human or animal in need of said treatment.

DESCRIPTION OF PREFERRED FEATURES

One class of pro-drugs of the invention, which is preferred on account of the relatively high activity of the parent compound, comprises isobutylgaba pro-drugs of the formula (IV)

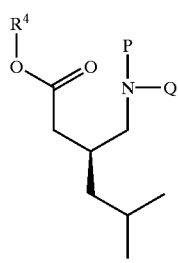

(IV)

in which P, Q and $R^4$ have the meanings given above, and pharmaceutically acceptable salts of any salt-forming compound within the above class.

Where $R^4$ is not hydrogen, it is desirable that it should be more labile than Q so that under physiological conditions the free acid forms first and unwanted reactions between the amino and carboxyl groups are avoided. Suitable values of $R^4$ other than hydrogen are ethyl, iso-propyl, benzyl, phenyl, methyl and t-butyl.

The group Q may be one which can be removed hydrolytically under physiological conditions, in which case it may be

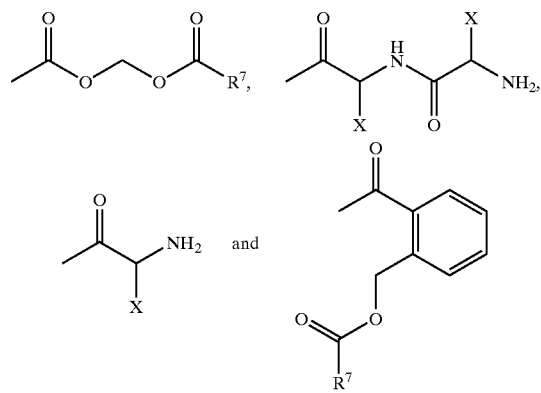

in which:

$R^5$ is hydrogen, straight or branched chain $C_1$–$C_6$ alkyl, phenyl or benzyl in which the benzene ring may be substituted or unsubstituted; and Y is hydrogen, straight or branched chain $C_1$–$C_6$ alkyl, or —$CH_2CO_2R^6$ in which $R^6$ represents straight or branched chain $C_1$–$C_6$ alkyl Alternatively, the group Q may be one which can be removed enzymatically under physiological conditions, in which case it may be selected from in which:

$R^7$ is hydrogen, straight or branched chain, phenyl or benzyl in which either or each benzene ring may be substituted or unsubstituted; and X represents a phenyl group or any of the side chains of the 20 naturally encoded α-amino acids.

In a preferred group of compounds Q is

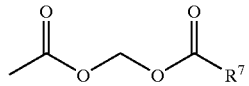

wherein $R^7$ is $C_1$–$C_6$ alkyl (preferably methyl or t-butyl) or phenyl.

Compounds according to the invention include inter alia:

(S)-3-(Benzoylaminomethyl)-5-methylhexanoic acid;

(S)-Benzyl 3-(acylaminomethyl)-5-methylhexanoate;

(S)-3-[N-(acetoxymethyleneoxycarbonyl)aminomethyl]-5-methylhexanoic acid;

(S)-3-[N-((2,2-dimethylpropionyloxy)methyleneoxycarbonyl)-aminomethyl]-5-methylhexanoic acid;

(S)-3-[N-(benzoyloxymethyleneoxycarbonyl)aminomethyl]-5-methylhexanoicacid; and pharmaceutically acceptable salts of any of the above.

Various methods may be used to prepare compounds according to the invention e.g. from starting materials disclosed in the patents referred to above.

For example, amide prodrugs of pregabalin may be prepared by reacting pregabalin with an acid chloride in an ether e.g. tetrahydrofuran at ambient temperatures. A carboxylic acid group of the resulting prodrug may be converted to an ester group by reaction with an alcohol e.g. by reaction with benzyl alcohol in the presence of 1,3-dicyclohexyldiimide (DCC) and 4-dimethylaminopyridine (DMAP) in a halogenated hydrocarbon solvent e.g. dichloromethane (DCM) at ambient temperatures. (Acyloxy)alkyl carbamate prodrugs of pregabalin may be prepared by reacting pregabalin with an acyloxyalkyl p-nitrophenyl carbonate in an ether e.g. tetrahydrofuran at ambient temperatures.

These reactions are illustrated in the following reaction scheme by reference to preferred reagents and preferred final products (4), (5) and (6), it being understood that a similar scheme applies mutatis mutandis to the use of other acyl chlorides, acyloxymethylene carbonates and optionally esterifying reagents, for the preparation of other final products of formula (III) above.

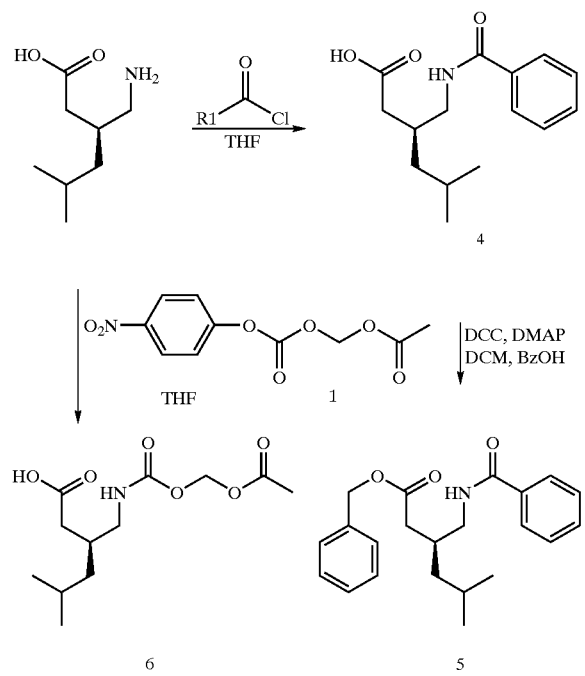

The compounds of the invention are expected to be useful in the treatment of epilepsy. They may also be used as mimetic agents for neurodegenerative disorders. Such neurodegenerative disorders are, for example, Alzheimer's disease, Huntington's disease, Parkinson's disease, and Amyotrophic Lateral Sclerosis. The present invention also covers treating acute brain injury. These include but are not limited to: stroke, head trauma, and asphyxia. Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia such as in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. Treatment with the present compounds could also be useful in a range of incidents, for example, during cardiac bypass surgery, in incidents of intracranial hemorrhage, in perinatal asphyxia, in cardiac arrest, and status epilepticus. A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

The present compounds are also expected to be useful in the treatment of anxiety and of panic as demonstrated by means of standard pharmacological procedures.

The compounds of the invention are also expected to be useful in the treatment of pain. Pain refers to acute as well as chronic pain. Acute pain is usually short-lived and is associated with hyperactivity of the sympathetic nervous system. Examples are postoperative pain and allodynia. Chronic pain is usually defined as pain persisting from 3 to 6 months and includes somatogenic pains and psychogenic pains. Other pain is nociceptive. Still other pain is caused by injury or inflammation of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from. Psychogenic pain is that which occurs without an organic origin such as low back pain, atypical facial pain, and chronic headache. Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

The present compounds are also expected to be useful in the treatment of digestive disorders such as visceral pain, pain associated with cancer, the irritable bowel syndrome, infection and inflammation.

The present compounds can be prepared and administered in a wide variety of oral and parenteral dosage forms. Thus, they can be administered by injection, that is, intravenously, intramuscularly, intracutaneously, subcutaneously, intraduodenally, or intraperitoneally. Also, they can be administered by inhalation, for example, intranasally. Additionally, the compounds of the present invention can be administered transdermally. It will be obvious to those skilled in the art that the following dosage forms may comprise as the active component either a compound of the invention or a corresponding pharmaceutically acceptable salt.

For preparing pharmaceutical compositions from the present compounds, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, binders, preservatives, tablet disintegrating agents, or an encapsulating material.

In powders, the carrier is a finely divided solid that is in a mixture with the finely divided active component. In tablets, the active component is mixed with the carrier having the necessary binding properties in suitable proportions and compacted in the shape and size desired. The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol.

Aqueous solutions suitable for oral use can be prepared by dissolving the active component in water and adding suitable colorants, flavours, stabilising and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilised in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day, if desired.

Preparation of Reagents
Acetoxymethyl p-nitrophenyl Carbonate (1)

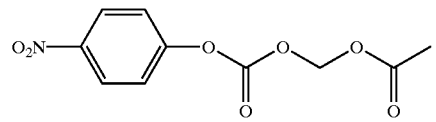

Carbonate 1 was prepared as described in *J.Med.Chem*, 1988, 31, 318–322 (5.29 g, 98%). Its characteristics were described in *J.Org.Chem*, 1997, 62, 1356–1362.

$v_{max}$(film)/cm$^{-1}$ 1776 (C=O), 1526 (C=C, Ar).
$\delta_H$(400 MHz; CDCl$_3$) 2.19 (3H, s, CH$_3$), 5.88 (2H, s, OCH$_2$O), 7.42 (2H, d, J 9.6, p-NO$_2$ArH), 8.30 (2H, d, J 9.2, p-NO$_2$ArH).

2,2-dimethylpropionyloxymethyl p-nitrophenyl Carbonate (2)

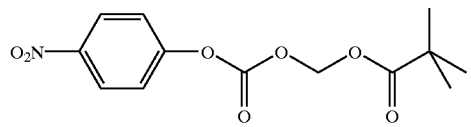

Carbonate 2 was also prepared as described in the above paper (1.16 g, 60%).

$v_{max}$(film)/cm$^{-1}$ 1779, 1759 (C=O), 1530 (C=C, Ar).
$\delta_H$(400 MHz; CDCl$_3$) 1.26 (9H, s, $^t$butyl), 5.89 (2H, s, OCH$_2$O), 7.41 (2H, d, J 9.4, p-NO$_2$ArH), 8.30 (2H, d, J 9.2, p-NO$_2$ArH).

Benzoyloxymethyl p-nitrophenyl Carbonate (3)

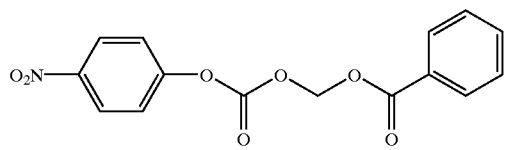

Carbonate 3 was also prepared as described in the above paper (1.76 g, 85%).

$v_{max}$(film)/cm$^{-1}$ 1778, 1740 (C=O), 1525 (C=C Ar).
$\delta_H$(400 MHz; CDCl$_3$) 6.14 (2H, s, OCH$_2$O), 7.42 (2H, d, J 9.2, p-NO$_2$ArH), 7.49 (2H, t, J 8.0, ArH), 7.64 (1H, t, J 7.6, ArH), 8.12 (2H, d, J 7.2, ArH) 8.29 (2H, d, J 9.2, p-NO$_2$ArH).

The invention will now be further described with reference to the following Examples.

EXAMPLE 1

(S)-3-(Benzoylaminomethyl)-5-methylhexanoic Acid (4)

Benzoyl chloride (0.88 ml, 7.6 mmol) was added to a stirred suspension of pregabalin (1.0 g, 6.3 mmol) in THF (80 ml) at room temperature under argon and the reaction mixture was stirred for 18 hours. The reaction mixture was then filtered and concentrated in vacuo. The residue was chromatographed (SiO$_2$, heptane-ethyl acetate, 1:1 to 3:7) to give 4 (0.78 g, 47%).

$\nu_{max}$(film)/cm$^{-1}$ 1705, 1634 (C=O), 1547 (C=C, Ar).

$\delta_H$(400 MHz; CDCl$_3$) 0.92 (3H, d, J 6.8, CH$_3$), 0.94 (3H, d, J 7.6, CH$_3$), 1.20–1.30 (2H, m, CH$_2$CH(CH$_3$)$_2$), 1.69–1.79 (1H, m, CH(CH$_3$)$_2$), 2.20–2.30 (1H, m, CHCH$_2$CH(CH$_3$)$_2$), 2.35 (1H, dd, J 8.1, 14.7, CH$_A$H$_B$COOH), 2.45 (1H, dd, J 14.7, 4.2, CH$_A$H$_B$COOH), 3.38–3.43 (1H, m, CH$_A$H$_B$NH), 3.57–3.63 (1H, m, CH$_A$H$_B$NH), 6.63 (1H, bs, NH), 7.41–7.57 (3H, m, ArH), 7.78 (2H, d, J 7.6, ArH).

EXAMPLE 2

(S)-Benzyl 3-(benzoylaminomethyl)-5-methylhexanoate (5)

Benzyl alcohol (0.31 g, 3.0 mmol) was added to a stirred mixture of (S)-3-(benzoylaminomethyl)-5-methylhexanoic acid 4 (0.78 g, 3.0 mmol), 1,3-dicyclo-hexylcarbodiimide (0.61 g, 3.0 mmol), and 4-dimethylaminopyridine (0.36 g, 3.0 mmol) in dichloromethane (40 ml) and the mixture was stirred for 18 hours. The reaction mixture was, filtered and concentrated in vacuo. The residue was chromatographed (SiO$_2$, heptane-ether, 1:0 to 75:25) to give 5 (0.83 g, 79%).

$\nu_{max}$(film)/cm$^{-1}$ 1732, 1640 (C=O).

$\delta_H$(400 MHz; CDCl$_3$) 0.89 (3H, d, J 7.2, CH$_3$), 0.91 (3H, d, J 6.8, CH$_3$), 1.19–1.30 (2H, m, CH$_2$CH(CH$_3$)$_2$), 1.64–1.75 (1H, m, CH(CH$_3$)$_2$)2.23–2.35 (1H, m, CHCH$_2$CH (CH$_3$)$_2$), 2.39 (1H, dd, J 15.4, 7.3, CH$_A$H$_B$COOH), 2.47(1H, dd, J 15.4, 4.9, CH$_A$H$_B$COOH), 3.34–3.39 (1H, m, CH$_A$H$_B$NH), 3.52–3.58 (1H, m, CH$_A$H$_B$NH), 5.08 (2H, s, ArCH$_2$O), 6.64 (1H, bt, NH), 7.27–7.38 (5H, m, ArH), 7.39–7.50 (3H, m, ArH), 7.75 (2H, d, J 7.2, ArH).

EXAMPLE 3

(S)-3-[N-(acetoxymethyleneoxycarbonyl)aminomethyl]-5-methylhexanoic Acid (6)

The carbonate 1 (1.0 g, 3.9 mmol) and pregabalin (0.62 g, 3.9 mmol) were stirred in THF (60 ml) at room temperature for 48 hours. The reaction mixture was taken up in ethyl acetate (250 ml) and washed with water (200 ml), 1N HCl (200 ml), dried (MgSO$_4$) and concentrated in vacuo. The residue was purified by column chromatography (SiO$_2$, heptane, then heptane-ethyl acetate, 1:1) to give (6) (0.18 g, 17%).

$\nu_{max}$(film)/cm$^{-1}$ 1715 (C=O).

$\delta_H$(400 MHz; CDCl$_3$) 0.91 (3H, d, J 6.8, CH$_3$), 0.91 (3H, d, J 6.8, CH$_3$), 1.10–1.30 (2H, m, CH$_2$CH(CH$_3$)$_2$), 1.60–1.71 (1H, m, CH(CH$_3$)$_2$), 2.12 (3H, s, COCH$_3$), 2.15–2.35 (1H, m, CHCH$_2$CH(CH$_3$)$_2$), 2.27 (1H, dd, J 15.0, 8.0, CH$_A$H$_B$COOH), 2.37 (1H, dd, J 14.8, 4.4, CH$_A$H$_B$COOH), 3.10–3.17 (1H, m, CHHNH), 3.30–3.36 (1H, m, CHHNH), 5.28 (1H, bs, NH), 5.71 & 5.75 (OCH$_2$O).

From reagents 2 and 3 there may correspondingly be prepared (S)-3-[N-((2,2-dimethylpropionyloxymethylenoxy)carbonyl)aminomethyl)-5-methyl-hexanoic acid and (S)-3-[N-(benzoyloxymethyleneoxycarbonyl) aminomethyl]-5-methylhexanoic acid.

What is claimed is:

1. A compound of the formula (IV)

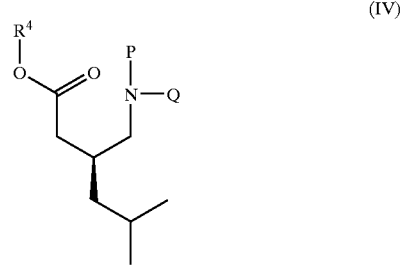

(IV)

in which:

R$^4$ is hydrogen or a labile ester-forming group selected from substituted and unsubstituted C$_1$–C$_6$ alkyl, benzyl and phenyl groups that become removed in the human or animal body;

P is hydrogen or methyl;

Q is selected from

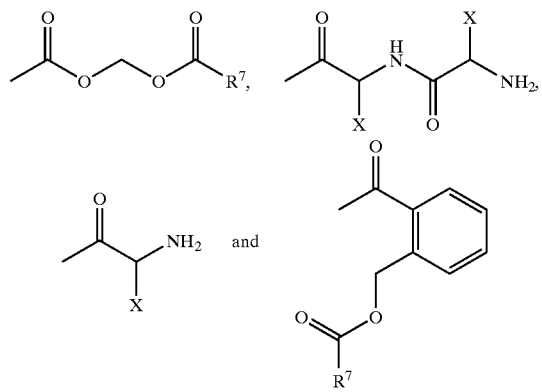

in which;

R$^7$ is hydrogen, straight or branched chain C$_1$–C$_6$ alkyl, phenyl or benzyl in which either or each benzene ring may be substituted or unsubstituted; and X represents a phenyl group or any of the side chains of the 20 naturally encoded α-amino acids; or a pharmaceutically acceptable salt of any salt-forming compound within the above class.

2. A compound of the formula (III)

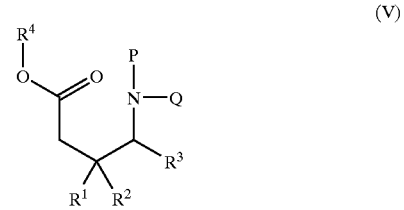

(V)

in which:

P is hydrogen or methyl;

R$^1$ is straight or branched C$_2$–C$_6$ alkyl, C$_3$–C$_6$ cycloalkyl or phenyl;

R$^2$ is hydrogen or methyl; and

R$^3$ is hydrogen, methyl or carboxyl; and

R$^4$ is hydrogen or a labile ester-forming group selected from substituted and unsubstituted C$_1$–C$_6$ alkyl, benzyl and phenyl groups that become removed in the human or animal body;

Q is selected from

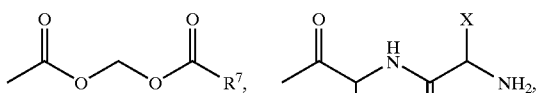
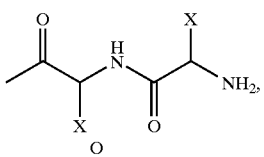
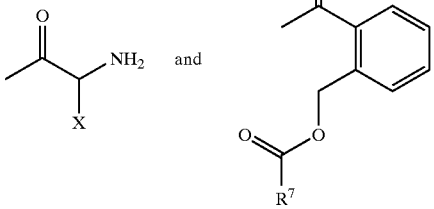

in which:

R⁷ is hydrogen, straight or branched chain $C_1$–$C_6$ alkyl, phenyl or benzyl in which either or each benzene ring may be substituted or unsubstituted; and X represents a phenyl group or any of the side chains of the 20 naturally encoded α-amino acids; or a pharmaceutically acceptable salt of any salt-forming compound within the above class, but excluding compounds in which $R_1$ is phenyl and $R^2$, $R^3$ and $R^4$ are each hydrogen.

3. The compound of claim 2, wherein Q is

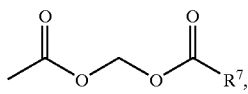

wherein $R^7$ is methyl, t-butyl or phenyl.

4. The compound of claim 1, wherein Q is

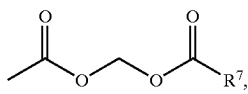

wherein $R^7$ is methyl, t-butyl or phenyl.

5. A compound selected from (S)-3-(Benzoylaminomethyl)-5-methylhexanoic acid;
(S)-Benzyl-3-(acylaminomethyl)-5-methylhexanoate;
(S)-3-[N-(acetoxymethylneoxycarbonyl)aminomethyl]-5-methylhexanoic acid;
(S)-3-[N-((2,2-dimethylpropionyloxy)methyleneoxycarbonyl)-amino-methyl]-5-methylhexanoic acid;
(S)-3-[N-(benzoyloxymethyleneoxycarbonyl)aminomethyl]-5-methyl-hexanoic acid; and
pharmaceutically acceptable salts of any of the above.

6. A method for making a compound of the formula (III) or salt thereof, as defined in claim 2, which comprises:

coupling a compound of the formula:

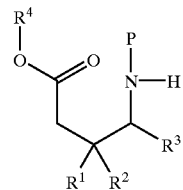

(V)

in which P and $R^1$–$R^4$ have the meanings given in claim 2 and in which said compound is in the form of a free base or an ammonium salt with a compound of the formula

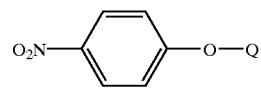

or QCl where Q has the meaning given in claim 1.

7. The method of claim 6, in which the compound (V) is a carboxylic acid and comprising the further step of esterifying the carboxyl group with a substituted or unsubstituted $C_1$–$C_6$ alkanol, benzyl alcohol or phenol.

8. A pharmaceutical composition comprising a pharmaceutically acceptable carrier and a therapeutically effective amount of a compound of the formula (III)

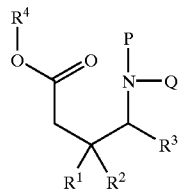

(III)

in which:

P is hydrogen or methyl;

$R^1$ is straight or branched $C_2$–$C_6$ alkyl, $C_3$–$C_6$ cycloalkyl or phenyl;

$R^2$ is hydrogen or methyl; and $R^3$ is hydrogen, methyl or carboxyl; and $R^4$ is hydrogen or a labile ester-forming group selected from substituted and unsubstituted $C_1$–$C_6$ alkyl, benzyl and phenyl groups that become removed in the human or animal body, Q is selected from

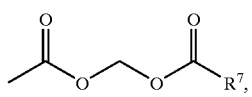
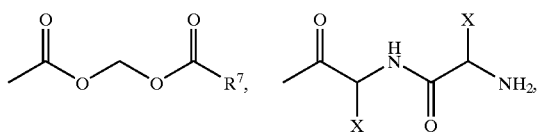

-continued

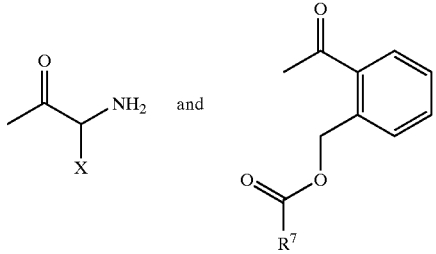

in which:

R⁷ is hydrogen, straight or branched chain $C_1$–$C_6$ alkyl, phenyl or benzyl in which either or each benzene ring may be substituted or unsubstituted; and X represents a phenyl group or any of the side chains of the 20 naturally encoded α-amino acids;

or a pharmaceutically acceptable salt of any salt-forming compound within the above class, but excluding compounds in which $R_1$ is phenyl and $R^2$, $R^3$ and $R^4$ are each hydrogen.

9. A method for treating epilepsy comprising administering a therapeutically effective amount of a compound according to claim 1 to a human or animal in need of said treatment.

10. A method for treating faintness attacks, hypokinesia and cranial disorders comprising administering a therapeutically effective amount of a compound according to claim 1 to a human or animal in need of said treatment.

11. A method for treating a neurodegenerative disorder comprising administering a therapeutically effective amount of a compound according to claim 1 to a human or animal in need of said treatment.

12. A method for treating depression comprising administering a therapeutically effective amount of a compound according to claim 1 to a human or animal in need of said treatment.

13. A method for treating anxiety comprising administering a therapeutically effective amount of a compound according to claim 2 to a human or animal in need of said treatment.

14. A method for treating panic comprising administering a therapeutically effective amount of a compound according to claim 2 to a human or animal in need of said treatment.

15. A method for treating pain comprising administering a therapeutically effective amount of a compound according to claim 2 to a human or animal in need of said treatment.

16. A method for treating a neuropathological disorder comprising administering a therapeutically effective amount of a compound according to claim 2 to a human or animal in need of said treatment.

17. A method for treating a digestive disorder corn rising administering a therapeutically effective amount of a compound according to claim 2 to a human or animal in need of said treatment.

* * * * *

UNITED STATES PATENT AND TRADEMARK OFFICE
CERTIFICATE OF CORRECTION

PATENT NO. : 6,703,522 B2
DATED : March 9, 2004
INVENTOR(S) : David Clive Blakemore et al.

It is certified that error appears in the above-identified patent and that said Letters Patent is hereby corrected as shown below:

Column 10,
Line 18, "from substituted and unsubstiruted $C_1$-$C_6$ alkyl, benzyl" should read
-- from substituted and unsubstituted $C_1$-$C_6$ alkyl, benzyl --
Line 48, "A compound of the formula (III)" should read -- A compound of the formula (V) --

Column 12,
Line 24, "or QCI where Q has the meaning given in claim 1." should read -- or QCI where Q has the meaning given in claim 2. --

Column 13,
Line 25, "according to claim 1 to a human or animal in need of said" should read
-- according to claim 2 to a human or animal in need of said --
Line 30, "1 to a human or animal in need of said treament." should read -- "2 to a human or animal in need of said treatment. --

Column 14,
Line 3, "of a compound according to claim 1 to a human or animal" should read -- of a compound according to claim 2 to a human or animal --
Line 7, "according to claim 1 to a human or animal in need of said" should read
-- according to claim 2 to a human or animal in need of said --
Line 24, "A method for treating a digestive disorder corn rising" should read -- A method for treating a digestive disorder comprising --

Signed and Sealed this

Fifth Day of July, 2005

JON W. DUDAS
*Director of the United States Patent and Trademark Office*